United States Patent
Hurt

[11] 3,975,420
[45] Aug. 17, 1976

[54] O,S-DIALKYL O-SULFONYLOXY-PHENYL PHOSPHOROTHIOLATES AND PHOSPHORODITHIOATES

[75] Inventor: William S. Hurt, Collegeville, Pa.

[73] Assignee: Rohm and Haas Company, Philadelphia, Pa.

[22] Filed: May 12, 1975

[21] Appl. No.: 576,838

Related U.S. Application Data

[63] Continuation-in-part of Ser. No. 519,448, Oct. 31, 1974, abandoned.

[52] U.S. Cl. .......................... 260/456 P; 424/215
[51] Int. Cl.² .................................. C07C 143/68
[58] Field of Search ........................... 260/456 P

[56] References Cited
OTHER PUBLICATIONS
Nippon, Chem. Abstract, 71, 2186n (1969).
Ishida et al., Chem. Abstract, 70, 57397j (1969).

Primary Examiner—James O. Thomas, Jr.
Assistant Examiner—Nicky Chan
Attorney, Agent, or Firm—Betty A. Narducci

[57] ABSTRACT

This invention relates to novel organophosphorothiolates and phosphorodithioates of the formula:

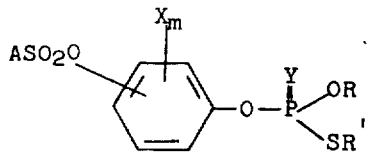

wherein R is a $(C_1-C_4)$ alkyl group;
R' is a $(C_3-C_6)$ alkyl group;
Y is an oxygen atom or sulfur atom;
X is a halogen atom, a $(C_1-C_5)$ alkyl group, or a $(C_1-C_5)$ alkoxy group;
m is an integer from 0 to 3; and
A is
  a. a $(C_1-C_5)$ alkyl group optionally substituted with up to three halogen atoms;
  b. a $(C_5-C_6)$ cycloalkyl group;
  c. a $(C_7-C_{10})$ aralkyl group, the aryl portion of which is optionally substituted with up to three halogen atoms, nitro groups, $(C_1-C_5)$ alkyl groups, or $(C_1-C_5)$ alkoxy groups; or
  d. an aryl group of the formula:

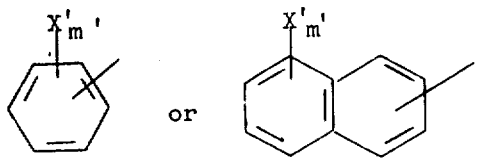

wherein X is a halogen atom, a nitro group, a $(C_1-C_5)$ alkyl group, or a $(C_1-C_5)$ alkoxy group; and
m' is an integer from 0 to 3;
to compositions containing them and to methods of using them to control pests.

8 Claims, No Drawings

O,S-DIALKYL O-SULFONYLOXY-PHENYL PHOSPHOROTHIOLATES AND PHOSPHORODITHIOATES

This application is a continuation-in-part of U.S. Ser. No. 519,448 filed Oct. 31, 1974, now abandoned.

The present invention relates to novel organophosphorothiolates and phosphorodithioates, having pesticidal activity, especially acaricidal and insecticidal activity, to compositions containing them, and to methods of using them to control various harmful pests. In addition to possessing outstanding pesticidal activity, compounds of the present invention possess a combination of desirable characteristics not possessed by known organophosphorus pesticides. These characteristics include activity against organophosphorus resistant species, residual activity, low toxicity to warm-blooded animals and low phytotoxicity for economically important plant species.

These novel compounds can be represented by the formula:

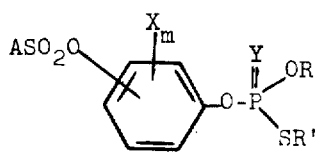
(I)

wherein
R is a $(C_1-C_4)$ alkyl group, preferably methyl or ethyl, most preferably ethyl;
R' is a $(C_3-C_6)$ alkyl group, preferably a $(C_3-C_5)$ alkyl group of the formula:

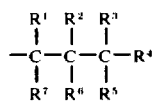

wherein
$R^1-R^7$ are individually hydrogen, methyl, or ethyl, preferably hydrogen;
Y is an oxygen atom or a sulfur atom, preferably an oxygen atom,
X is a halogen atom, preferably chlorine; a $(C_1-C_5)$ alkyl group, preferably methyl; or a $(C_1-C_5)$ alkoxy group, preferably methoxy;
m is an integer from 0 to 3; and
A is
a. a $(C_1-C_5)$ alkyl group optionally substituted with up to three halogen atoms, preferably chlorine;
b. a $(C_5-C_6)$ cycloalkyl group;
c. a $(C_7-C_{10})$ aralkyl group, preferably benzyl, the aryl portion of which is optionally substituted with up to three nitro groups; halogen atoms, preferably chlorine; $(C_1-C_5)$ alkyl groups, preferably methyl; or $(C_1-C_5)$ alkoxy groups, preferably methoxy; or
d. an aryl group of the formula:

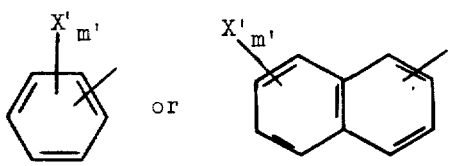

wherein
X' is a halogen atom; a nitro group; a $(C_1-C_5)$ alkyl group preferably methyl; or a $(C_1-C_5)$ alkoxy group, preferably methoxy; and
m' is an integer from 0 to 3.

As used in the specification and claims, the terms "alkyl" "alkoxy" and "aralkyl" are intended to include branched chain as well as straight chain groups. Representative alkyl groups include methyl, ethyl, n-propyl, sec-butyl, isobutyl, pentyl, neopentyl, 2-methylpentyl, n-hexyl and the like. Representative alkoxy groups include methoxy, ethoxy, propoxy, sec-butoxy, pentoxy and the like. Representative aralkyl groups include benzyl, phenethyl, 3-phenyl-1-methylpropyl, and the like.

The organophosphorothiolates and phosphorodithioates described above can exist in their isomeric forms, wherein the $ASO_2O$-group of Formula I is attached to the benzene ring in a position which is ortho, meta or para to the point of attachment of the phosphorothiolate or phosphorodithioate group.

In a preferred embodiment of this invention, the compounds can be represented by the formula:

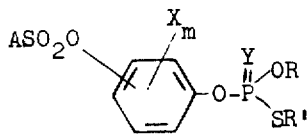
(II)

wherein
R, R' and Y are as defined for Formula I;
X is a halogen atom, preferably chlorine; or a $(C_1-C_5)$ alkyl group, preferably methyl;
m is an integer from 0 to 2;
A is
a. a $(C_1-C_5)$ alkyl group optionally substituted with a chlorine atom,
b. a benzyl group, or
c. an aryl group of the formula:

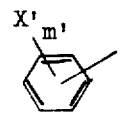

wherein
X' is a bromine, chlorine or fluorine atom; a nitro group; or a $(C_1-C_5)$ alkyl group, preferably methyl;
m' is an integer from 0 to 2;
and the $ASO_2O$— group is attached to the benzene ring in a position which is meta or para to the point of attachment of the phosphorothiolate or phosphorodithioate group.

Typical compounds within the scope of this invention include:

O-Methyl O-[4-(methanesulfonyloxy)phenyl] S-n-propyl phosphorothiolate

O-[4-(trichloromethanesulfonyloxy)phenyl] O-ethyl S-n-propyl phosphorothiolate

O-ethyl O-[3-(isopropanesulfonyloxy)phenyl] S-n-propyl phosphorothiolate

O-[3-(n-butanesulfonyloxy)phenyl] O-ethyl S-n-propyl phosphorothiolate

O-Ethyl S-isobutyl O-[2-(n-pentanesulfonyloxy)phenyl] phosphorodithioate

O-[3-(cyclohexanesulfonyloxy)phenyl] O-ethyl S-n-propyl phosphorothiolate

O-Ethyl S-n-propyl O-[4-(α-toluenesulfonyloxy)phenyl] phosphorothiolate

O-[4-(3',4'-dichloro-α-toluenesulfonyloxy)phenyl] O-ethyl S-isobutyl phosphorothiolate O-[4-(4'-chlorobenzenesulfonyloxy)phenyl] O-ethyl S-isobutyl phosphorothiolate O-Ethyl S-n-propyl O-[4-(p-toluenesulfonyloxy)phenyl] phosphorothiolate O-[3-(benzenesulfonyloxy)phenyl] S-n-butyl O-ethyl phosphorothiolate O-[3-(benzenesulfonyloxy)phenyl] S-sec-butyl O-ethyl phosphorothiolate O-[3-(benzenesulfonyloxy)phenyl] O-ethyl S-isobutyl phosphorothiolate O-[2-(benzenesulfonyloxy)phenyl] O-ethyl S-n-pentyl phosphorothiolate O-Ethyl O-[4-(4'-fluorobenzenesulfonyloxy)phenyl] S-isobutyl phosphorothiolate O-Ethyl O-[3-(4'-nitrobenzenesulfonyloxy)phenyl] phosphorothiolate O-Ethyl S-isobutyl O-[3-(3'-nitrobenzenesulfonyloxy)phenyl] phosphorothiolate O-Ethyl O-[3-(2'-nitrobenzenesulfonyloxy)phenyl] S-n-propyl phosphorothiolate O-Ethyl S-isobutyl O-[4-(2', 4', 5'-trichlorobenzenesulfonyloxy)phenyl] phosphorothiolate O-Ethyl S-n-propyl O-[4-(p-toluenesulfonyloxy)-2,5-dichlorophenyl] phosphorothiolate O-[3-(4'-chlorobenzenesulfonyloxy)-4,6-dichlorophenyl] O-ethyl S-n-propyl phosphorothiolate S-sec-Butyl O-ethyl O-[4-(methanesulfonyloxy)phenyl] phosphorothiolate O-Methyl O-[4-(4'-methoxybenzenesulfonyloxy)phenyl] S-n-propyl phosphorothiolate O-[4-(4'-chloro-2'-methylbenzenesulfonyloxy)phenyl]O-ethyl S-n-propyl phosphorothiolate O-[4-(benzenesulfonyloxy)-2-methylphenyl]O-ethyl S-isobutyl phosphorothiolate O-[3-benzenesulfonyloxy)-2,5-dimethylphenyl] O-ethyl S-n-propyl phosphorothiolate O-[2-(benzenesulfonyloxy)-4-methoxyphenyl] O-methyl S-n-propyl phosphorothiolate O-n-Butyl O-[4-(4'-chloro-2-naphthalenesulfonyloxy)phenyl] S-n-propyl phosphorothiolate O-[4-(5',7'-dimethyl-2-naphthalenesulfonyloxy)-6-chlorophenyl] O-ethyl S-isobutyl phosphorothiolate O-Ethyl O-[4-(2-naphthalenesulfonyloxy)phenyl] S-n-propyl phosphorodithioate O-Ethyl O-[4-(methanesulfonyloxy)phenyl] S-n-propyl phosphorodithioate O-[3-(benzenesulfonyloxy)phenyl] S-sec-butyl O-ethyl phosphorodithioate The compounds of this invention can be prepared by reacting a phenol with an O,S-dialkylphosphorochloridothiolate or phosphorochloridodithioate. The general reaction can be represented by the following equation:

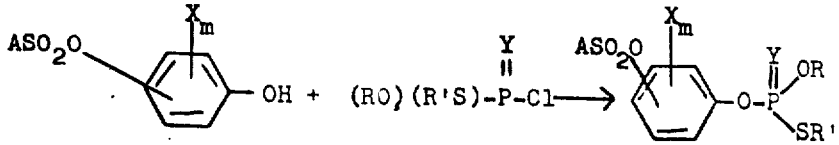

wherein A, Y, R, R', X and m are as defined for Formula I.

An acid acceptor such as a tertiary amine or an alkali carbonate or hydroxide can be employed as a scavenger in the preparation. Representative acid acceptors include pyridine, trimethylamine, triethylamine, dimethylaniline, lithium carbonate, sodium hydroxide, potassium hydroxide and the like. Generally, a substantially equimolar ratio of reactants is preferred but an excess of any of the reactants can be employed. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile, and the like. Suitable solvents include benzene, toluene, heptane, methylethyl ketone, acetone, ethyl ether, acetonitrile and dioxane. The reaction is generally conducted in a temperature range of about −10° to about 100° C. or more, and preferably in the range of about 0° to about 60° C.

In addition to the above procedure, the compounds of this invention can be prepared by reacting an alkali phenoxide with an O,S-dialkylphosphorochloridothiolate or phosphorochloridodithioate. The reaction can be represented by the following equation:

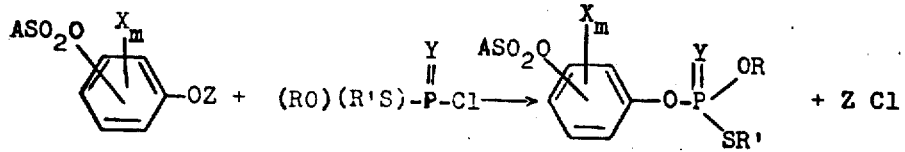

wherein A, R, R', X, Y and m are as defined for Formula I and Z is an alkali metal, such as sodium, potassium or lithium.

Reaction conditions, including choice of solvents, temperature, and molar ratios correspond to the conditions described above for the reaction of an O, S-dialkylphosphorochloridothiolate or phosphorochloridodithioate with a phenol, except that there is no need to emply an acid acceptor in this reaction.

All of the starting materials used in the preparation of the compounds of this invention are known compounds or are readily prepared by adaptations of known routes. For example, arylsulfonyloxy phenols and alkanesulfonyloxy phenols are prepared by selective hydrolysis of bis-arylsulfonates and bis-alkylsulfonates respectively [E. Kampouris, *J. Chem. Soc.*, 2651 (1965); B. Helferich and P. Papalambrou, *Ann.*, 551 235 (1942)]. The O,S-dialkylphosphorochloridothiolates are prepared by reacting an alkylsulfenylchloride with a dialkylchlorophosphite [A. F. Lippman, *J. Org. Chem.*, 30, 3217 (1965)].

The following examples are given by way of illustration and are not to be considered as limitations of the present invention. Examples 1 to 23 are illustrative preparations of starting materials useful in the synthesis of compounds of this this invention. The remaining Examples are illustrative preparations of compounds listed in Table I below.

EXAMPLE 1

Preparation of 3-(methanesulfonyloxy)phenol

A mixture of 50.0 g. (0.188 mole) of bis-(1,3-methanesulfonyloxy) benzene and 1 liter of methanol is warmed to 40° C. until the solution becomes homogenous and then cooled to 23°C. A solution of potassium hydroxide, 24.7 g. (0.37 mole) in 100 ml. of 10% aqueous methanol is added dropwise with stirring at 23°C. After stirring for four days at room temperature, a copious amount of a precipitate (potassium methane sulfonate) forms, and is removed by filtration.

The filtrate is concentrated in vacuo to give a mixture of an oil and a solid. The residue is taken up in 500 ml. of water, extracted once with 200 ml. of toluene to remove neutral products, and then acidified to pH <1 with 50 ml. of concentrated hydrochloric acid whereupon a precipitate, 3-(methanesulfonyloxy)phenol, is observed. The phenol is collected by filtration, washed with water, and air dried to give 15.8 g. (45%) of product, m.p. = 78°–80°C. The filtrate is extracted 3 times with 100 ml. portions of methylene chloride. The extracts are combined, dried over sodium sulfate and concentrated in vacuo to give an additional 11.5 g. (33%) of 3-(methanesulfonyloxy)phenol, m.p. 77–80°C.

EXAMPLE 2 – 22

In a manner similar to that of Example 1, the following compounds are likewise readily prepared:

| Compounds | m.p. (b.p.)°C. |
|---|---|
| 4-(methanesulfonyloxy)phenol | 75–76° |
| 2-(methanesulfonyloxy)phenol | (105°/0.1 mm) |
| 4-(n-butanesulfonyloxy)phenol | (155°/0.2 mm) |
| 3-(chloromethanesulfonyloxy)phenol | 64.8–67.0 |
| 4-(ethanesulfonyloxy)phenol | Oil |
| 2,4-dichloro-5-(methanesulfonyloxy)phenol | 136.5–137.5° |
| 2,5-dichloro-4-(methanesulfonyloxy)phenol | 129.8–130.9° |
| 3-(3'-chloropropanesulfonyloxy)phenol | Oil |
| 4-(benzenesulfonyloxy)phenol | 75.5–76.5° |
| 3-(benzenesulfonyloxy)phenol | 89–90° |
| 4-(p-toluenesulfonyloxy)phenol | 94–95.5° |
| 4-(4'-chlorobenzenesulfonyloxy)phenol | 99–101° |
| 4-(α-toluenesulfonyloxy)phenol | (155°/0.12 mm) |
| 3-(4'-nitrobenzenesulfonyloxy)phenol | 126–128.5° |
| 3-(4'-fluorobenzenesulfonyloxy)phenol | 78.5–79.5° |
| 4-(4'-bromobenzenesulfonyloxy)phenol | 105–107.9° |
| 3-(2'-nitrobenzenesulfonyloxy)phenol | Oil |
| 3-(methanesulfonyloxy)5-methylphenol | Oil |
| 3-(3'-nitrobenzeneslfonyloxy)phenol | Oil |
| 3-(2',4'-dimethylbenzenesulfonyloxy)phenol | 79.5–81.0 |
| 3-(isopropaneslfonyloxy)phenol | |

EXAMPLE 23

Preparation of 3-(3',4'-dichlorobenzenesulfonyloxy)phenol

A mixture of 200 ml. of 48% aqueous hydrobromic acid and 18.8 g. (0.056 mole) 3-(3',4'-dichlorobenzenesulfonyloxy) anisole is stirred under reflux (116°C.) for 7 days. The solution is then cooled to 0° – 10°C. and made basic to pH 12 with 300 ml. of 30% sodium hydroxide. The basic solution is extracted with 200 ml. of benzene to remove neutral products and then acidified to pH <1 with 10 ml. of concentrated hydrochloric acid. The aqueous solution is extracted three times with 150 ml. portions of chloroform. The chloroform extracts are combined, dried over sodium sulfate and concentrated in vacuo to give 5.9 g. (33%) of 3-(3',4'-dichlorobenzenesulfonyloxy) phenol as a crystalline solid; m.p. = 107°–109.5°C.

EXAMPLE 24

Preparation of O-ethyl O-[4-(methanesulfonyloxy)phenyl] S-n-propyl phosphorathiolate To a solution of 3.5 g. (0.019 mole) of p-(methanesulfonyloxy)phenol in 150 ml. of anhydrous acetonitrile is added in portions, 0.81 g. (0.02 mole) of sodium hydride (57% in mineral oil) at 5° C. The slurry is stirred until no further hydrogen is evolved, and then 3.75 g. (0.019 mole) of O-ethyl S-n-propyl phosphorochloridothiolate is added dropwise with stirring at 5° C. over a period of 10 minutes. The slurry is then stirred for two days at room temperature, filtered to remove sodium chloride and mineral oil and concentrated in vacuo to give 6.1 g. (93%) of the desired product as a yellow oil.

EXAMPLE 25

Preparation of O-ethyl O-[2-(methanesulfonyloxy)phenyl] S-n-propyl phosphorothiolate A dispersion of sodium hydride, 0.90 g. (0.0376 mole) in 20 ml. of acetonitrile is added in portions to a stirring solution of 7.08 g (0.0376 mole) of 2-(methanesulfonyloxy)-phenol, in 100 ml. of acetonitrile at room temperature. The slurry is stirred until no further gas is evolved and then 7.62 g. (0.0367 mole) of O-ethyl S-n-propyl phosphorochloridothiolate is added dropwise at room temperature. The mixture is stirred overnight and the concentrated in vacuo. The residue is taken up in 100 ml. of benzene, washed once with water, dried over sodium sulfate and concentrated in vacuo to give the phosphorothiolate as an oil. The oil is further purified by chromatography on silica gel using butyl acetate/heptane as the eluent to give 7.0 g. (52%) of the phosphorothiolate as a pale yellow oil.

EXAMPLE 27

Preparation of O-ethyl O-[3-(methanesulfonyloxy)phenyl] S-n-propyl phosphorothiolate A dispersion of sodium hydride, 0.74 g. (0.030 mole) in 20 ml. of acetonitrile is added in portions to a stirring solution of 5.3 g. (0.028 mole) of 3-(methanesulfonyloxy)-phenol in 100 ml. of acetonitrile at room temperature. The slurry is stirred until no further gas is evolved and then 5.7 g (0.028 mole) of O-ethyl S-n-propyl phosphorochloridothiolate is added dropwise at room temperature. The mixture is stirred overnight and then concentrated in vacuo. The residue is taken up in 100 ml. of benzene, washed once with water, dried over sodium sulfate and concentrated in vacuo to give 8.1 g. (91%) of the phosphorothiolate as an oil. The oil is further purified by chromatography as described in Example 25. nmr (CDCl$_3$) δ= 0.97(3H,t,C$\underline{H}_3$), 1.42(3H, t, C$\underline{H}_3$), 1.75(2H, m,CH$_2$C$\underline{H}_2$CH$_3$), 2.92(2H,m,SC$\underline{H}_2$CH$_2$CH$_3$), 3.10(3H,s,SO$_2$C$\underline{H}_3$), 4.35 (2H,m,OC$\underline{H}_2$CH$_3$), 7.1 – 7.6(4H,m,aromatic)

EXAMPLE 29

Preparation of O-ethyl S-isobutyl
O-[3-(methanesulfonyloxy)phenyl] phosphorothiolate A solution of 4.09 g. (0.022 mole) of 3-(methanesulfonyloxy)phenol in 30 ml. of acetonitrile is added dropwise to a stirring suspension of 0.57 g. (0.024 mole) of sodium hydride in 120 ml. of acetonitrile at 22° – 26°C. The solution is warmed to 40°C. until the evolution of gas ceases and then 5.1 g. (0.024 mole) of O-ethyl S-isobutyl phosphorochloridothiolate is added dropwise. The mixture is stirred overnight and then filtered to removed sodium chloride. The filtrate is concentrated in vacuo. The residue is taken up in 100 ml. of toluene, washed twice with 100 ml. portions of water, dried over sodium sulfate, filtered through 10 g. of silica gel and concentrated in vacuo to give 4.1 g (51%) of the phosphorothiolate as a pale yellow oil: nmr $(CDCl_3)\delta=$ 1.02(6H,d,—CH$(CH_3)_2$), 1.43(3H,t,OC$H_2$C$H_3$), 1.92(1H,m,SCH$_2$C$H$(CH$_3$)$_2$), 2.88(2H,m,SC$H_2$CH<), 3.18(3H,s,SO$_2$C$H_3$), 4.35(2H,m,OC$H_2$CH$_3$), 6.95–7.60(4H,m,aromatic).

EXAMPLE 31

Preparation of S-sec-butyl O-ethyl
O-[3-(methanesulfonyloxy)phenyl] phoshorothiolate This compound is prepared and purified according to the procedure described in Example 29. S-sec-butyl O-ethyl phosphorothiolate, 5.1 g. 0.024 mole), is used as the phoshorylating agent to give 4.1 g. (51%) of the desired phosphorothiolate as a yellow oil: nmr (CDCl$_3$) $\delta$ = 0.92(3H,$\underline{m}$,—CH$_2$CH$_3$), 1.15–1.90(8H,m,SCH(C$H_3$), C$H_2$ CH$_3$ and OCH$_2$C$H_3$), $\delta$=3.12(3H,s,SO$_2$C$H_3$), 3.40(1H,m,SC$H$(CH$_3$)CH$_2$—), 4.30(2H,m,OC$H_2$—CH$_3$), 7.10–7.60(4H,m,aromatic).

EXAMPLE 32

Preparation of
O-[3-(chloromethanesulfonyloxy)-phenyl] O-ethyl
S-n-propyl phoshorothiolate A solution of 4.0 g. (0.018 of 3-(chloromethanesulfonyloxy)phenol in 50 ml. of acetonitrile is added dropwise to 0.47 g. (0.020 mole) of sodium hydride in 150 ml. of toluene. The mixture is stirred until no further hydrogen is evolved, and then 4.01 g. (0.020 mole) of O-ethyl S-n-propyl phosphorochloridothiolate is added dropwise. The solution is stirred overnight at room temperature and then filtered to remove sodium chloride. The filtrate is washed and concentrated as described in Example 29 to give 4.1 g. (53%) of the crude phosphorothiolate which is further purified by chromatography to give the pure product: nmr (CDCl$_3$) $\delta$=0.98(3H,t,C$H_3$), 1.42(3H,t,C$H_3$), 1.61(2H,m,SCH$_2$C$H_2$CH$_3$), 2.90(2H,m,SC$H_2$CH$_2$CH$_3$), 4.30(2H,m,OC$H_2$CH$_3$), 4.80(2H,s,ClC$H_2$SO$_2$), 7.05–7.55(4H, aromatic.

EXAMPLE 35

Preparation of O-[3-(methanesulfonyloxy)-phenyl]
O-methyl S-n-propyl phosphorothiolate This compound is prepared and purified according to the procedure described in Example 29, by using 4.42 g. (0.024 mole) of 3-(methanesulfonyloxy)phenol, 0.62 g. (0.026 mole) sodium hydride, and 4.87 g. (0.026 mole) of O-methyl S-n-propyl phosphorochloridothiolate to give 3.9 g. (49%) of the phosphorothiolate as a light green oil: nmr (CDCl$_3$) $\delta$ = 0.93(3H,t,CH$_2$C$H_3$), 1.69(2H,M,SCH$_2$C$H_2$CH$_3$), 2.85(2H,m,SC$H_2$—CH$_2$—), 3.82(3H,d,OC$H_3$), 6.95–7.50(4H,m,aromatic).

EXAMPLE 36

Preparation of O-ethyl
O-[4-(methanesulfonyloxy)phenyl]S-n-propyl phosphorodithioate This compound is prepared and purified according to the procedure described in Example 29 by using. 2.54 g. (0.0135 mole) of 4-(methanesulfonyloxy)phenol, 0.35 g. (0.015 mole) of sodium hydride and 3.3 g. (0.015 mole) of O-ethyl S-n-propyl phosphorochlorididothioate, to give 2.4 g. (48%) of the phosphorodithioate as a green oil after chromatography: nmr (CDCl$_3$) $\delta$=0.98(3H,t,—CH$_2$C$H_3$), 1.37(3H,T,OCH$_2$C$H_3$), 1.70(2H,m,SCH$_2$ C$H_2$CH$_3$), 2.83(2H,m,SC$H_2$CH$_2$—), 3.10(3H,s,SO$_2$C$H_3$), 4.20(2H,m,OC$H_2$CH$_3$), 7.12(4H,s,aromatic).

EXAMPLE 39

Preparation of O-[4-(benzenesulfonyloxy)phenyl]
O-ethyl S-n-propyl phosphorothiolate To a solution of 7.5 g. (0.03 mole) of p-(benzenesulfonyloxy) phenol in 40 ml. of anhydrous acetonitrile is added a dispersion of 0.75 g. (0.03 mole) of sodium hydride (mineral oil free) in 20 ml. of acetonitrile at 25°–40° C. Then 6.4 g. (0.03 mole) of O-ethyl S-n-propyl phosphorochloridothiolate is added dropwise at 40° C. and the resulting slurry held at 45° C. for 18 hours after which it is vacuum filtered to remove sodium chloride. The filtrate is diluted with 100 ml. of benzene and 50 ml. of hexane and washed three times with water. The organic phase is dried over sodium sulfate, filtered through a bed of silica gel and concentrated in vacuo to give 9.2 g. (73%) of the desired product as a pale yellow oil. The oil is further purified by chromatography on silica gel using butyl acetate/heptane as the eluent.

EXAMPLE 40

Preparation of O-[3-(benzenesulfonyloxy)-phenyl]
O-ethyl S-n-propyl phosphorothiolate Sodium hydride, 0.64 g. (0.027 mole) in 20 ml. of acetonitrile is added in portions to a stirring solution of 6.3 g. (0.025 mole) of 3-(benzenesulfonyloxy)phenol in 50 ml. of acetonitrile at 3°–40°C. The slurry is warmed to 60°C., held at that temperature until no further hydrogen gas is evolved and then recooled to 30° C. O-ethyl S-propyl phosphorochloridothiolate, 6.3 g. (0.026 mole) is added dropwise at 30°–40° C. and the slurry is left stirring overnight at 30° C. The mixture is then filtered through a short column of silica gel and the filtrate concentrated in vacuo to give 10.0 g. (96%) of the phosphorothiolate as a deep amber oil. The oil is further purified by chromatography as described in Example 39 to give 6.0 g. of the pure product as a pale yellow oil.

EXAMPLE 41

Preparation of O-ethyl
O-[4-(4'-methylbenzenesulfonyloxy)phenyl]
S-n-propyl phosphorothiolate This compound is prepared and purified according to the procedure described in Example 40 by using 7.2 g.

(0.027 mole) of 4-(4'-methylbenzenesulfonyloxy)-phenol to give 11.5 g. (98%) of the crude phosphorothiolate as a yellow oil and 7.0 g. (60%) of the pure phosphorothiolate as a pale yellow oil after chromatography.

EXAMPLE 43

Preparation of O-ethyl S-n-propyl O-[4-(α-toluenesulfonyloxy)phenyl] phosphorothiolate A dispersion of sodium hydride, 0.61 g. (0.025 mole) in 20 ml. of acetonitrile is added in portions to a solution of 6.2 g. (0.02 mole) of 4-(α-toluenesulfonyloxy)-phenol in 100 ml. of acetonitrile. The mixture is stirred until no further hydrogen gas is evolved. Then, O-ethyl S-n-propyl phosphorochloridothiolate, 4.7 g. (0.023 mole) is added dropwise at room temperature. The solution is stirred at room temperature for two days, filtered to remove sodium chloride, and concentrated in vacuo to give 10.2 g. (102%) of the phosphorothiolate as a brown oil which is further purified by chromatography as described in Example 39: nmr $(CDCl_3) \delta = 0.95$ (3H,t,$CH_3$), 1.37(CH,t,$CH_3$), 1.68(2H,m,$SCH_2CH_2CH_3$), 2.88(2H,m,$SCH_2CH_2CH_3$), 4.26(2H,m,$OCH_2CH_3$), 4.55(2H,s,$CH_2$), 6.98–7.50 (9H, aromatic).

EXAMPLE 44

Preparation of O-[3-(3',4'-dichlorobenzenesulfonyloxy)phenyl] O-ethyl S-n-propyl phosphorothiolate A suspension of 0.44 (0.018 mole) of sodium hydride in 30 ml. of acetonitrile is added in portions to a stirring solution of 5.3 g. (0.016 mole) of 3-(3',4'-dichlorobenzenesulfonyloxy)phenol in 120 ml. of acetonitrile at room temperature. When there is no further evidence of gas evolution, 3.34 g. (0.016 mole) of O-ethyl S-n-propyl phosphorochloridothiolate is added dropwise. The mixture is stirred at room temperature for two days, filtered to remove sodium chloride and concentraed in vacuo to give 7.3 g. (91%) of the phosphorothiolate as a yellow oil. A portion of the oil (4.0 g.) is further purified by chromatography as described in Example 39 to give 1.7 g. of the pure product.

EXAMPLE 49

Preparation of O-ethyl O-[3-(3'-nitrobenzenesulfonyloxy)phenyl] S-n-propyl phosphorothiolate A solution of 5.1 g. (0.017 mole) of 3-(3'-nitrobenzenesulfonyloxy)phenol in 30 ml. of acetonitrile is added dropwise to a stirring suspension of 0.46 g. (0.019 mole) of sodium hydride in 120 ml. of acetonitrile at 21°–26°C. The mixture is warmed to 45° C. and held until no further gas is evolved. Then, 3.86 g. (0.019 mole) of O-ethyl S-n-propyl phosphorochloridothiolate in 30 ml. of acetonitrile is added dropwise at 36°–37°C. The mixture is stirred overnight at room temperature and then filtered to removed sodium chloride. The filtrate is concentrated in vacuo to give 7.3 g. (91%) of the product as a dark oil which is further purified by chromatography as described in Example 39 to give 1.8 g. of the pure phosphorothiolate: nmr $(CDCl_3)$ $\delta = 0.95(3H,t,-CH_2CH_3)$, 1.38(3H,t,$OCH_2CH_3$), 1.67(2H,m,$SCH_2CH_2CH_3$), 2.82(2H,m,$SCH_2CH_2-$), 4.28(2H,m,$OCH_2CH_3$), 6.8–8.8(8H,m,aromatic).

EXAMPLE 51

Preparation of O-[4-(benzenesulfonyloxy)-phenyl] O-methyl S-n-propyl phosphorothiolate The compound is prepared and purified according to the procedure described in Example 49 by using 3.7 g. (0.015 mole) of 4-(benzenesulfonyloxy)phenol, 0.39 g. (0.016 mole) of sodium hydride and 3.09 g. (0.016 mole) of O-methyl S-n-propyl phosphorochloridothiolate to give 5.0 g. (83%) of the phosphorothiolate as a dark oil. A portion of the oil is further purified by chromatography as described in Example 39, to give the product as a light yellow oil: nmr $(CDCl_3)$, $\delta = 0.95(3H,t,-CH_2CH_3)$, 1.61(2H,m,$SCH_2CH_2CH_3$), 2.85(2H,m,$SCH_2CH_2-$), 3.88(3H, d,$OCH_3$), 7.00(4H,m,aromatic), 7.67(5H,m,aromatic).

In a manner-similar to the foregoing Examples, the following compounds are likewise readily prepared:

Example 33

Preparation of S-n-butyl O-ethyl O-[3-(methanesulfonyloxy)phenyl] phosphorothiolate Yield = 40%. nmr $(CDCl_3)$ $\delta = 0.98(3H,t,-CH_2CH_3)$, 1.50(3H,t,$OCH_2CH_3$) 1.25–2.10(4H,m,$-SCH_2CH_2CH_2CH_3$), 3.07(2H,m,$SCH_2CH_2-$), 4.35(2H,m,$OCH_2CH_3$), 7.10–7.60(4H,m,aromatic).

EXAMPLE 34

Preparation of O-[4-(ethanesulfonyloxy)phenyl] O-ethyl S-n-propyl phosphorothiolate Yield = 49%: nmr $(CDCl_3)$ $\delta = 0.98(3H,t,-CH_2CH_3)$, 1.20–1.98(8H,m,$SCH_2CH_2CH_3,OCH_2CH_3$, $SO_2CH_2CH_3$), 2.90(2H,m,$SCH_2CH_2-$), 3.18(2H,q,$SO_2CH_2CH_3$), 4.30(2H,m,$OCH_2CH_3$), 7.17(4H,s,aromatic).

EXAMPLE 37

Preparation of O-Ethyl O-[3-(methanesulfonyloxy)-5-methylphenyl] S-n-propyl phosphorothiolate Yield = 86%: nmr $(CDCl_3)$ $\delta = 0.98(3H,t,CH_3)$, 1.43 (3H,t,$OCH_3CH_3$), 1.71(2H,m,$SCH_2CH_2CH_3$), 2.35(3H,s,$CH_3$), 2.85 (2H,m,$SCH_2CH_2-$), 4.27(2H,m,$OCH_2CH_3$), 7.03(3H, aromatic).

EXAMPLE 38

Preparation of O-[3-(3'-chloropropanesulfonyloxy)phenyl] O-ethyl S-n-propyl phoshorothiolate Yield = 19%. nmr $(CDCl_3)$ $\delta = 0.98$ (3H,t,$-CH_2CH_3$), 1.40(3H,t,$OCH_2CH_3$), 1.72(2H,m,$SCH_2CH_2CH_3$), 2.50(2H,m,$SO_2CH_2CH_2CH_2Cl$), 2.90(2H,m,$SCH_2CH_2-$), 3.48(2H,t,$SO_2CH_2CH_2-$), 3.70(2H,t,$ClCH_2CH_2-$), 4.30(2H,m,$OCH_2CH_3$), 7.05–7.60(4H,m,aromatic).

EXAMPLE 46

Preparation of O-ethyl O-[3-(4'-fluorobenzenesulfonyloxy)phenyl] S-isobutyl phosphorothiolate Yield = 100%: nmr $(CDCl_3)$ $\delta = 0.99(6H,d,-CH(CH_3)_2)$, 1.41(3H,$OCH_2CH_3$), 1.87(2H,m,—CH$_2$CH(CH$_3$)$_2$), 2.78(2H,d of d,SCH$_2$CH<), 4.30(2H,m,OCH$_2$CH$_3$), 6.72–7.48(6H,m,aromatic), 7.85(2H,m,aromatic).

Example 47

Preparation of O-[4-(4'-bromobenzenesulfonyloxy)phenyl] S-sec-butyl O-ethyl phosphorothiolate Yield = 97%: nmr (CDCl$_3$) δ=0.95(3H,m,CH$_3$), 1.20–1.85 (8H,m,SCH(CH$_3$) CH$_2$CH$_3$ and OCH$_2$CH$_3$).

3.36(1H,m,SCH(CH$_3$)CH$_2$—), 4.30(2H,m,OCH$_2$CH$_3$), 7.15(4H,m,aromatic), 7.73(4H,s,aromatic).

EXAMPLE 48

Preparation of O-ethyl S-isobutyl O-[3-(2'-nitrobenzenesulfonyloxy)phenyl] phosphorothiolate Yield = 70%: nmr (CDCl$_3$) δ=0.99(6H,d,—CH(CH$_3$)$_2$), 1.41(3H,t,OCH$_2$CH$_3$), 1.89(1H,m,SCH$_2$CH(CH$_3$)$_2$), 2.77(2H,d of d, SCH$_2$CH<), 4.30(2H,m,OCH$_2$CH$_3$), 7.12(4H,m,aromatic), 7.88(4H,m,aromatic). aromatic).

EXAMPLE 50

Preparation of O-ethyl O-3-(2,4-dimethylbenzenesulfonyloxy)phenyl] S-n-propyl phosphorothiolate Yield = 94%: nmr (CDCl$_3$) δ = 0.95(3H,t,—CH$_2$CH$_3$), 1.40(3H,t,OCH$_2$CH$_3$), 1.68(2H,m,SCH$_2$CH$_2$CH$_3$), 2.39(3H,s,CH$_3$), 2.71(3H,s,CH$_3$), 2.90(2H,m,SCH$_2$CH$_2$—), 4.30(2H,m,OCH$_2$CH$_3$), 6.90–7.90(7H,m,aromatic).

TABLE I

ELEMENTAL ANALYSIS ETC.*

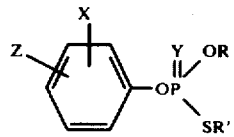

| Ex. No. | Z | X | R | R' | Y | ANALYSIS CALCULATED (FOUND) | | | |
|---|---|---|---|---|---|---|---|---|---|
| | | | | | | C | H | P | S |
| 24 | 4-CH$_3$SO$_2$O— | H | C$_2$H$_5$ | C$_3$H$_7$n | O | | | | |
| 25 | 2-CH$_3$SO$_2$O— | H | C$_2$H$_5$ | C$_3$H$_7$n | O | 40.7 (40.6) | 5.40 (5.49) | 8.74 (8.70) | 18.1 (18.1) |
| 26 | 4-n-C$_4$H$_9$SO$_2$O— | H | C$_2$H$_5$ | C$_3$H$_7$n | O | 45.4 (45.5) | 6.36 (6.48) | 7.81 (7.55) | — |
| 27 | 3CH$_3$SO$_2$O— | H | C$_2$H$_5$ | C$_3$H$_7$n | O | 40.7 (40.7) | 5.40 (5.64) | 8.74 (8.68) | — |
| 28 | 4-CH$_3$SO$_2$O— | 2,5-diCl | C$_2$H$_5$ | C$_3$H$_7$n | O | 34.1 (34.3) | 4.05 (4.40) | 7.32 (7.33) | — |
| 29 | 3-CH$_3$SO$_2$O— | H | C$_2$H$_5$ | C$_4$H$_9$iso | O | | | | |
| 30 | 3-CH$_3$SO$_2$O— | 4,6-diCl | C$_2$H$_5$ | C$_3$H$_7$n | O | 34.1 (34.7) | 4.05 (4.11) | 7.32 (6.65) | — |
| 31 | 3-CH$_3$SO$_2$O— | H | C$_2$H$_5$ | C$_4$H$_9$sec | O | | | | |
| 32 | 3-ClCH$_2$SO$_2$O— | H | C$_2$H$_5$ | C$_3$H$_7$n | O | | | | |
| 33 | 3-CH$_3$SO$_2$O— | H | C$_2$H$_5$ | C$_4$H$_9$n | O | | | | |
| 34 | 4-C$_2$H$_5$SO$_2$O— | H | C$_2$H$_5$ | C$_3$H$_7$n | O | | | | |
| 35 | 3-CH$_3$SO$_2$O— | H | CH$_3$ | C$_3$H$_7$n | O | | | | |
| 36 | 4-CH$_3$SO$_2$O— | H | C$_2$H$_5$ | C$_3$H$_7$n | S | | | | |
| 37 | 3-CH$_3$SO$_2$O | 5-CH$_3$ | C$_2$H$_5$ | C$_3$H$_7$n | O | | | | |
| 38 | 3-ClCH$_2$CH$_2$CH$_2$SO$_2$O— | H | C$_2$H$_5$ | C$_3$H$_7$n | O | | | | |
| 39 | 4-(φSO$_2$O—) | H | C$_2$H$_5$ | C$_3$H$_7$n | O | | | | |
| 40 | 3-(φSO$_2$O—) | H | C$_2$H$_5$ | C$_3$H$_7$n | O | 49.0 (48.8) | 5.08 (5.11) | 7.44 (7.44) | 15.4 (15.8) |
| 41 | 4-(4'-CH$_3$φSO$_2$O—) | H | C$_2$H$_5$ | C$_3$H$_7$n | O | 50.2 (50.4) | 5.38 (5.32) | 7.20 (7.05) | 14.9 (14.8) |
| 42 | 4-(4'-ClφSO$_2$O—) | H | C$_2$H$_5$ | C$_3$H$_7$n | O | 45.3 (45.2) | 4.47 (4.42) | 6.87 (7.19) | 14.2 (14.1) |
| 43 | 4-(φCH$_2$SO$_2$O—) | H | C$_2$H$_5$ | C$_3$H$_7$n | O | | | | |
| 44 | 3-(3',4'-diClφSO$_2$O—) | H | C$_2$H$_5$ | C$_3$H$_7$n | O | 42.1 (43.2) | 3.94 (4.37) | 6.38 (6.29) | |
| 45 | 3-(4'-NO$_2$φSO$_2$O—) | H | C$_2$H$_5$ | C$_3$H$_7$n | O | 44.3 (44.8) | 4.37 (4.64) | 6.71 (6.98) | |
| 46 | 3-(4'-FφSO$_2$O—) | H | C$_2$H$_5$ | C$_4$H$_9$iso | O | | | | |
| 47 | 4-(4'-BrφSO$_2$O—) | H | C$_2$H$_5$ | C$_4$H$_9$sec | O | | | | |
| 48 | 4-(2'-NO$_2$φSO$_2$O—) | H | C$_2$H$_5$ | C$_4$H$_9$iso | O | | | | |
| 49 | 3-(3'-NO$_2$φSO$_2$O—) | H | C$_2$H$_5$ | C$_3$H$_7$n | O | | | | |
| 50 | 3-(2',4'-diCH$_3$φSO$_2$O—) | H | C$_2$H$_5$ | C$_3$H$_7$ | O | | | | |
| 51 | 4-(φSO$_2$O—) | H | CH$_3$ | C$_3$H$_7$ | O | | | | |
| 52 | 4-(φSO$_2$O—) | H | C$_2$H$_5$ | C$_3$H$_7$ | S | | | | |

*Structures of examples lacking analytical data were confirmed by nmr.

The organophosphorothiolates and phosphorodithioates of this invention possess general utility as arthropodicides, particularly against members of the class Arachnoidea, which includes the order Acarina, as represented by mites and ticks, and Insecta, the insects. Certain compounds of this invention are also active as nematocides, ovicides, larvicides, and fungicides, particularly phytopathogenic fungicides.

Initial evaluations are made on the following mite, insects and nematode:

| Code Symbol | Common Name | Latin Name |
|---|---|---|
| TSM | Two-spotted spider mite | *Tetranychus urticae* |
| GPA | Green peach aphid | *Myzus persicae* |
| BB | Mexican bean beetle | *Epilachna varivestis* |

| Code Symbol | Common Name | Latin Name |
|---|---|---|
| AW | Southern armyworm | Spodoptera eridania |
| BW | Boll weevil | Anthonomus grandis |
| LST | Lone star tick | Amblyoma americanum |
| HF | House fly | Musca domestica |
| SF | Stable fly | Stomoxys calcitrans |
| Nema | Southern root knot nematode | Meloidogyne incognita |

A test solution containing 600 ppm of test compound can be made by dissolving the test compound in a solvent (acetone: methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyd resin (commercially available under the trademark Triton B-1956) can be utilized at the equivalent of one ounce per gallon of test solution as a surfactant.

For the mite test, infested bean (*Phaseolus limeanus*) leaf discs (1.25 inches in diameter) containing about 50 mites and for green peach aphid tests, infested broccoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper paper are sprayed as above for the mite test in similar dishes and allowed to dry. One such dish is infested with 10 third instar Mexican bean beetle larvae, while another is infested with 10 third instar southern armyworm larvae. The dishes are covered. After holding for 48 hours, the percent kill is obtained.

For the boll weevil and house fly tests, half pint glass canning jars with a screened top are used. Food is supplied for the boll weevil (apple) and for the house fly (sugar water). The test insects consist of 10 adult boll weevils and 20 adult house flies. The jars containing the insects are sprayed using the turntable. The percent kill of boll weevil is determined 48 hours after the application. In the house fly test, a percent knockdown is determined one hour after application, the percent kill after 24 hours.

For the tick test, plastic Petri dish bottoms containing a piece of filter paper are sprayed with the test compounds. After the filter paper dries, a small quantity of water is pipetted into each dish to insure proper humidity. The dishes are then infested with about 50 lone star tick larvae and capped with tight-fitting plastic lids. After holding for 24 hours, the percent kill is obtained.

For the stable fly test, glass Mason half-pint jars with a piece of filter paper covering the bottom of each jar, are infested with 20, 3–5 day old male and female stable flies. Screening, held in place with screw-cap lids, is used to confine the flies. The jars containing the flies are sprayed directly on a turntable sprayer. The flies are held at 80° F. and 55% relative humidity for a one hour knock-down (KD) and 24-hour mortality observation. Results are recorded as the number of flies knocked down or dead per total number.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (*Cucumis sativus*) seeds are planted. About 23 days thereafter, the cucumber plants are removed from the soil and the root system examined for the presence of knots. A total of 25 knots or less is considered as a measure of control.

Table II gives the results of the foregoing biological evaluations.

TABLE II

ACARICIDAL, INSECTICIDAL, and NEMATOCIDAL DATA
% Control, etc. at 600 ppm.

| Ex. No. | TSM | GPA | BB | AW | BW | LST | House Fly KD | House Fly KILLED | Stable Fly KD | Stable Fly KILLED | Nema[b] |
|---|---|---|---|---|---|---|---|---|---|---|---|
| 24 | 100 | 100 | 100 | 100 | 80 | 100 | 100 | 100 | 100 | 100 | + |
| 25 | 100 | 100 | 100 | 100 | 100 | 100 | 100 | 100 | 25 | 100 | + |
| 26 | 100 | 100 | 100 | 100 | 20 | 90 | 100 | 100 | 100 | 100 | + |
| 27 | 100 | 100 | 100 | 100 | 100 | 90 | 85 | 100 | 75 | 100 | + |
| 28 | 100 | 100 | 100 | 100[a] | 100 | NT | 100 | 100 | 100 | 100 | − |
| 29 | 100 | 100 | 100 | 100[a] | 100 | NT | 100 | 100 | 100 | 100 | + |
| 30 | 100 | 100 | 100 | 100 | 100 | NT | 100 | 100 | 100 | 100 | − |
| 31 | 100 | 100 | 100 | 100 | 100 | NT | 100 | 100 | 100 | 100 | + |
| 32 | 100 | 100 | 100 | 100 | 80 | NT | 100 | 100 | 0 | 95 | + |
| 33 | 100 | 69 | 100 | 100 | 40 | NT | 60 | 60 | 0 | 70 | + |
| 34 | 100 | 100 | 100 | 100 | 0 | NT | 100 | 100 | 100 | 100 | + |
| 35 | 100 | 100 | 100 | 100 | 80 | NT | 100 | 100 | 30 | 100 | NT |
| 36 | 100 | 100 | 100 | 100 | 60 | NT | 100 | 100 | 0 | 100 | NT |
| 37 | 100 | 78 | 100 | 100 | 40 | NT | 90 | 100 | 30 | 100 | NT |
| 38 | 100 | 100 | 100 | 100 | 40 | NT | 100 | 100 | 100 | 100 | NT |
| 39 | 100 | 100 | 100 | 100 | 60 | 0 | 100 | 100 | 90 | 100 | + |
| 40 | 100 | 100 | 100 | 100 | 0 | 100 | 100 | 100 | 100 | 100 | + |
| 41 | 100 | 100 | 100 | 100 | 0 | 85 | 95 | 100 | 70 | 100 | − |
| 42 | 100 | 100 | 100 | 100 | 0 | 90 | 100 | 100 | 100 | 100 | + |
| 43 | 100 | 100 | 100 | 100 | 0 | 0 | 100 | 100 | 85 | 100 | + |
| 44 | 100 | 100 | 100 | 100 | 100 | 90 | 100 | 100 | 80 | 100 | + |
| 45 | 100 | 100 | 100 | 100[a] | 0 | NT | 45 | 90 | 75 | 100 | + |
| 46 | 100 | 100 | 100 | 100 | 60 | NT | 100 | 100 | 100 | 100 | + |
| 47 | 100 | 100 | 100 | 100 | 80 | NT | 100 | 100 | 100 | 100 | + |
| 48 | 100 | 100 | 100 | 100 | 100 | NT | 100 | 100 | 100 | 100 | NT |
| 49 | 100 | 100 | 100 | 100 | 100 | NT | 100 | 100 | 30 | 100 | NT |
| 50 | 100 | 100 | 100 | 100 | 60 | NT | 0 | 0 | 30 | 50 | NT |
| 51 | 100 | 100 | 100 | 100 | 20 | NT | 100 | 100 | 80 | 100 | NT |

TABLE II-continued

ACARICIDAL, INSECTICIDAL, and NEMATOCIDAL DATA
% Control, etc. at 600 ppm.

| Ex. No. | TSM | GPA | BB | AW | BW | LST | House Fly KD | House Fly KILLED | Stable Fly KD | Stable Fly KILLED | Nema[b] |
|---|---|---|---|---|---|---|---|---|---|---|---|
| 52 | 100 | 100 | 92 | 100 | 0 | NT | 40 | 100 | 0 | 85 | NT | a=percent control at 150 ppm.
b= + means control
    − means no control
NT=Not tested
KD=Knockdown Ovicidal and larvicidal tests are conducted on representative compounds of this invention. These compounds demonstrate ovicidal and larvicidal activity.

For mite tests involving the two-spotted mite ova and larvae, bean leaf sections containing about 100 eggs are placed on moistened cotton in a Petri dish and sprayed on the turntable with a 150 ppm test solution. These are held for 6 days and examined under the microscope. Unhatched eggs and dead and live larvae are counted and the percent ovicidal and larvicidal activity are determined.

For tests involving the southern corn rootworm (*Diabrotica undecimpunctata howardi*) ova and larvae, two layers of 4.25 cm. filter papers are placed in small, Petri dishes, and sprayed on the turntable with a 600 ppm solution of the test compound and air dried. About 100 eggs in about one milliliter of water are pipetted onto the filter paper and the dishes covered. These are held for 6 days and examined under the microscope. The percent kill values for ova and larvae are determined.

For the mosquito larvae test, approximately 20, 3-day old yellow fever mosquito larvae (*Aedes aegypti*) are introduced into styrofoam cups containing 100 ml. of water which has previously been treated with a test solution of selected compounds so as to give a 1 ppm concentration. Twenty-four hours later, the percent kill is determined.

Table II gives the results of these ovicidal and larvicidal tests.

TABLE III

OVICIDAL AND LARVICIDAL EVALUATIONS

| Ex. No. | Corn Rootworm at 600 ppm O | Corn Rootworm at 600 ppm L | Two Spotted Mite at 150 ppm O | Two Spotted Mite at 150 ppm L | Mosquito Larvae aT 1 ppm |
|---|---|---|---|---|---|
| 24 | 62 | 100 | 0 | 0 | 50 |
| 25 | 0 | 100 | 72 | 92 | 85 |
| 26 | 66 | 100 | 0 | 95 | 100 |
| 27 | 41 | 87 | 100 | — | 100 |
| 28 | NT | NT | NT | NT | 100 |
| 29 | 86 | 100 | NT | NT | 100 |
| 30 | 0 | 66 | NT | NT | 100 |
| 31 | 90 | 100 | NT | NT | 100 |
| 32 | 92 | 100 | NT | NT | 100 |
| 33 | 75 | 80 | NT | NT | 100 |
| 34 | 69 | 100 | NT | NT | 100 |
| 35 | 0 | 100 | NT | NT | 100 |
| 36 | 54 | 100 | NT | NT | NT |
| 37 | 62 | 100 | NT | NT | 100 |
| 38 | 0 | 100 | NT | NT | 100 |
| 39 | 59 | 100 | 55 | 100 | 100 |
| 40 | 0 | 100 | 0 | 100 | 100 |
| 41 | 0 | 100 | 36 | 93 | 100 |
| 42 | 40 | 96 | 64 | 69 | 100 |
| 43 | 29 | 100 | 50 | 50 | 100 |
| 44 | 0" | 30" | 43 | 93 | 100 |
| 45 | 50 | 93 | NT | NT | 100 |
| 46 | 0 | 100 | NT | NT | 100 |
| 47 | 54 | 100 | NT | NT | 100 |
| 48 | 47 | 100 | NT | NT | 100 |
| 49 | 0 | 100 | NT | NT | 100 |
| 50 | 0 | 88 | NT | NT | 100 |
| 51 | 0 | 100 | NT | NT | 100 |
| 52 | 0 | 100 | NT | NT | 100 |

NT=not tested

Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Some of the plant diseases controlled by compounds of this invention include the following:

| Code Symbol | Common Name | Latin Name |
|---|---|---|
| BPM | Bean Powdery Mildew | *Erysiphe polygoni* |
| GDM | Grape Downy Mildew | *Plasmopara viticola* |
| RB | Rice Blast | *Piricularia eryzae* |
| TLB | Tomato Late Blight | *Phytophthora infestans* |
| WLR | Wheat Leaf Rust | *Puccinia recondita* |

Table IV gives the results of the foregoing fungicidal evaluations.

TABLE IV

FUNGICIDAL DATA
Percent Kill
at 300 ppm

| EX. NO. | BPM | GDM | RB | TLB | WLR |
|---|---|---|---|---|---|
| 24 | E | E | B | E | E |
| 25 | E | B | A | NT | A |
| 27 | E | E | E | E | E |
| 39 | E | E | B | B | B |
| 40 | A | B | A | B | E |
| 41 | A | A | A | B | E |

NT=not tested

The compounds of the present invention are used for protection of plants and animals, including man, from the ravages of harmful and annoying pests or disease organisms which they may carry. The term "pest" as used herein is intended to include arthropods, such as insects and acarids in all stages of development, nematodes, fungi, such as phytopathogenic fungi, and the like. Generally, control of a living organism is achieved in accordance with this invention by application of the compounds in pesticidally effective amounts either directly to the pests to be controlled or to the loci to be freed of or protected from attack by such pests. For examaple, food, fiber, forage, forest, and ornamental crops and stored products thereof would represent plant protection loci. Treatment with compounds of this invention of domestic animals, man and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

For use as pesticides the compounds of this invention can be used as solutions in organic solvents or formulations. For example, they can be formulated as wettable powders, emulsifiable concentrates, dusts, granular formulations or flowable emulsifiable concentrates. In such formulations, the organophosphorothiolates or phosphorodithioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The organophosphorothiolate or phosphorodithioate can be taken up on or mixed with a finely particles solid carrier, as for example, clays, inorganic silicates, carbonates, and silicas. Organic carriers can also be employed. Dust concentrates are commonly made wherein organophosphorothiolates or phosphorodithioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The organophosphorothiolates or phosphorodithioates are usually present in the range of about 10 to about 80% by weight and surfactants form about 0.5 to about 10% by weight.

One convenient method for preparing a solid formulation is to impregnate the organophosphorothiolate or phosphorodithioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving organophosphorothiolates or phosphorodithioates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the organophosphorothiolate or phosphorodithioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form on substantially soluble in higher boiling solvents.

The application rate will, of course, vary depending upon the purposes for such application, the organophosphorothiolates or phosphorodithioates being utilized, the frequency of dissemination and the like.

By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

Many of the above formulations can be utilized on animals for control of parasites.

For use as insecticides and acaricides, dilute sprays can be applied at concentrations of about 0.001 to about 20 pounds of the active organophosphorothiolate phosphorodithioate ingredient per 100 gallons of spray. They are usually applied at about 0.01 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a nematocide or as a soil insecticide, the organophosphorothiolates or phosphorodithioates can be applied as a solid formulation, preferably a granular formulation, by broadcasting, side-dressing, soil incorporation or seed treatment. The application rate can be from about 1 to about 50 pounds per acre. For soil incorporation, the compounds of this invention can be mixed with the soil at a rate of about 2 to about 100 ppm.

For use as a fungicide, the organophosphorothiolates or phosphorodithioates can be applied as fungicidal sprays by methods commonly employed, such as conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to 50 lbs. per acre of the active ingredient. As a fungicidal seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula:

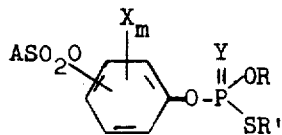

wherein
R is a ($C_1$–$C_4$) alkyl group;
R' is a ($C_3$–$C_8$) alkyl group;
Y is an oxygen atom or a sulfur atom;
X is a halogen atom, a ($C_1$–$C_5$) alkyl group, or a ($C_1$–$C_5$) alkoxy group;
m is an integer from 0 to 3; and
A is a ($C_1$–$C_5$) alkyl group.

2. A compound according to claim 1 wherein R' is a ($C_3$–$C_5$) alkyl group of the formula:

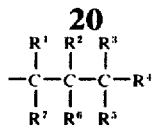

wherein $R^1$–$R^7$ are individually hydrogen, methyl, or ethyl.

3. A compound according to claim 2 wherein R is an ethyl group.

4. A compound according to claim 3 wherein X is a halogen atom, or a ($C_1$–$C_5$) alkyl group; m is an integer from 0 to 2.

5. A compound according to claim 4 having the formula:

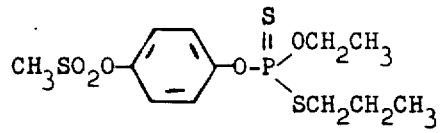

6. A compound according to claim 4 wherein Y is an oxygen atom.

7. A compound according to claim 6 having the formula:

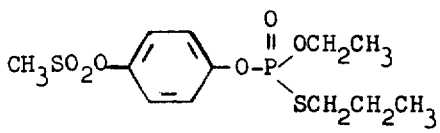

8. A compound according to claim 6 having the formula:

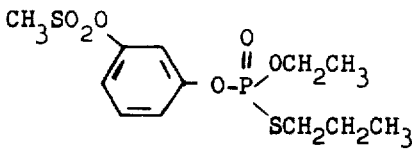

* * * * *